United States Patent [19]

Hammond et al.

[11] Patent Number: 5,089,403

[45] Date of Patent: Feb. 18, 1992

[54] PROCESS FOR ENZYMATIC HYDROLYSIS OF FATTY ACID TRIGLYCERIDES WITH OAT CARYOPSES

[75] Inventors: Earl G. Hammond; Inmok Lee, both of Ames, Iowa

[73] Assignee: Iowa State University Research Foundation, Inc., Ames, Iowa

[21] Appl. No.: 361,125

[22] Filed: Jun. 5, 1989

[51] Int. Cl.$^5$ ................................................. C12P 7/64
[52] U.S. Cl. ..................... 435/134; 435/198
[58] Field of Search ........................... 435/134, 198

[56] References Cited

FOREIGN PATENT DOCUMENTS

| 210893 | 11/1984 | Japan | 435/134 |
| 173791 | 8/1986 | Japan | 435/134 |
| 187796 | 8/1986 | Japan | 435/134 |
| 278988 | 12/1987 | Japan | 435/134 |
| 105683 | 5/1988 | Japan | 435/134 |

OTHER PUBLICATIONS

Frey et al., J. Am. Oil Chem. Soc., 52(9), 358-362 (1975).
Urquhart et al., CA 98: 177783g (1983).
Sahasrabudhe, J. Am. Oil Chem. Soc., 59(8), 354-55 (1982).
Hammond and Glatz, Food Biotechnology-2, pp. 205-209 (King and Chetham eds., Elsevir Science Publishers, 1988).
Hammond, E. G., Oat Lipids, Chapt. 16 in Lipids in Cereal Technology, Barnes ed. 1983, Academic Press, London.
Lee & Hammond, JAOCS, vol. 66, No. 4, p. 485 (Apr., 1989).

*Primary Examiner*—Carolyn Elmore
*Attorney, Agent, or Firm*—Tilton, Fallon, Lungmus & Chestnut

[57] ABSTRACT

Triglyceride oils are enzymatically hydrolyzed to fatty acids and glycerol by liquid phase contact with moistened dehulled oat seeds (oat caryopses). As produced, the fatty acids dissolve in the oil phase and the glycerol is absorbed into the caryopses which facilitates separation of the products of reaction. In a single contacting cycle, 20% or greater conversion of the triglyceride reactant can be obtained, and by cyclic or sequential contacting 50% or more of the oil reactant can be hydrolyzed.

10 Claims, No Drawings

PROCESS FOR ENZYMATIC HYDROLYSIS OF FATTY ACID TRIGLYCERIDES WITH OAT CARYOPSES

FIELD OF INVENTION

The field of this invention is the enzymatic hydrolysis of fatty acid triglycerides, such as the triglycerides present in vegetable or animal oils and fats. In particular, the invention is concerned with the use of lipases for splitting the triglycerides into free fatty acids and glycerine.

BACKGROUND OF INVENTION

Most industrial hydrolysis of fats and oils is carried out by the Colgate-Emery process of variations thereof, which splits the triglyceride esters by high pressure steam. [See, for example, Barnaby, et al. (1984), *J. Am. Oil Chem. Soc.*, 25:95-99.] Proposals have been made to replace this type of process with gentler and less energy-intensive enzymatic process. In particular, it has been proposed to use lipases for hydrolysis of fatty acid triglycerides. [See, for example, Linfield, et al. (1984), *J. Am. Oil. Chem. Soc.*, 61:191-195, and 1067-1071.]

The use of lipases for enzymatic hydrolysis of triglyceride fats and oils has been reviewed by Hammond, and Glatz pages 205-209, in "Food Biotechnology-2" (King and Chetham, eds., Elsevir Science Publishers, 1988). Very few enzymatic processes have gained commercial acceptance. Temperature sensitive oils, such as castor oil, which may be degraded by the high temperatures usually employed for steam hydrolysis have been commercially processed by lipases. [See Sonntag (1979), *J. Am. Oil. Chem. Soc.*, 56:729A; and Macrae (1985), *Biotech. Genetic. Eng. Rev.*, 3:193-217].

Lipase preparations can be obtained from various grains and seeds: Hassanien, et al. (1986), *J. Am. Oil. Chem. Soc.*, 63:893-897. Oat seeds are especially rich in lipase. The processing of oats usually begins with a steam treatment of the caryopses obtained after dehulling to deactivate the lipase. [See Hammond, E. G., "Oat Lipids", Chapt. 16, in "Lipids in Cereal Technology", Barnes, ed., 1983, Academic Press, London.] Oat lipase has been reviewed by Martin, et al. (1953), *Biochem.*, 55:523-529. Much of the lipase is on the surface of the oat caryopses, being removable by wet scrubbing of the caryopses surfaces.

SUMMARY OF INVENTION

The process of this invention utilizes dehulled oat seeds (oat caryopses) for enzymatic hydrolysis of fatty acid triglycerides to free fatty acids and glycerol (glycerine). The process is particularly applicable to vegetable oils but may also be applied to animal fats and fish oils.

Dehulled oat seeds (oat caryopses) having active lipase associated with their outer surfaces are hydrated prior to use in the process. The water content of the dehulled oat seeds is increased by 5 to 30% by weight to provide a total moisture content of 17 to 44%. The moistened oat caryopses are preferably substantially free of external water, are contacted with a liquid medium composed essentially of an oil phase containing the fatty acid triglyceride reactant as a principal component. The contacting is carried out at a temperature at which the oat lipase is enzymatically active and the contacting is continued until at least 20% by volume of the triglyceride reactant has been hydrolyzed.

One of the important features of the process is that an automatic partitioning is obtained between the split fatty acids and the glycerine by-product. The moistened seeds provide an internal aqueous phase which meets the external oil phase containing the triglyceride reactant at the outer surfaces of the seeds where the lipase is concentrated. As glycerol (glycerine) and free fatty acids are formed at this interface, the glycerol (glycerine) migrates into the water phase within the seeds while the fatty acids disperse in the external oil phase. Although this partitioning does not result in a 100% separation, most of the glycerol (glycerine) (up to 80-90%) enters the seeds, and substantially all of the fatty acids (up to 90-95%) dissolves in the external oil phase.

After completion of the reaction, the glycerol-containing oat seeds can be easily separated from the oil phase. The principal product, comprising the fatty acids, can be recovered from the separated oil phase. If desired, the glycerol can also be recovered from the seeds, or if recovery is not desired, the glycerol-containing seeds can be used as an animal feed. If the glycerol is removed, the seeds will still retain most of their nutrient value, and can be used as an animal feed.

As the hydrolysis proceeds, the products of the hydrolysis appear to inhibit the hydrolysis. Consequently, after hydrolyzing from 20 to 30% of the triglyceride reactant, it is desirable to remove the oat seed reactant and add a new increment of oat seeds to continue the hydrolysis. By using successive increments of oat seeds in this manner, conversion of the triglyceride reactant can be carried to a high yield, viz. conversions of 75 to 90% of triglyceride reactant. In the further incremental processing of the triglyceride reactant, it is not necessary to remove the fatty acids therefrom, the reaction can continue with the addition of fresh batches of the dehulled oat seeds. The glycerol produced in each reaction cycle is effectively removed by the separation of the batches of oat seeds.

DETAILED DESCRIPTION

The method of this invention can be employed with triglycerides composed of long-chain fatty acids, such as fatty acids containing from 4 to 22 carbons. Preferably, however, the method is applied to triglyceride oils composed predominately of fatty acids containing from 8 to 18 carbons.

In general, the method can be applied to triglyceride oils and fats obtained from vegetable or animal sources, such as vegetable oils, animal fats, and fish oils. The preferred vegetable oils include soybean, cottonseed, corn, linseed, coconut and palm. If the oil or fat reactant is a solid or has too high a viscosity at the temperatures desired for the hydrolysis reaction, the oil or fat can be thinned with an inert, non-toxic, organic solvent. Hydrocarbon solvents are particularly desirable, such as hexane.

Preferably, the oat seeds are freshly harvested and are selected to maximize the content of active lipase. After dehulling, the oat caryopses having active lipase associated with their outer surfaces are hydrated. Oats in the condition in which they are stored are usually referred to as "dry" oats, although they contain from 12 to 14% moisture. For purposes of the present invention, it is desirable to increase the moisture content of the oats by 5 to 30% by weight to provide a total moisture content of 17 to 44%. A preferred total moisture content is in the range from 30 to 40% by weight, or up to saturation of the caryopses. The oats may be soaked in water until they are essentially fully saturated, at which time they will typically have a water content of around 38 to 40%. The water may be applied by any suitable means such as soaking, spraying, etc. Following hydration, it is preferable to drain the seeds so that the oat seeds are substantially free of external water.

The hydration referred to above can be carried out at ordinary room temperatures, such as 20°–25° C. There does not appear to be any advantage in applying water to the oat seeds at higher temperatures, and it is desirable to avoid any water temperatures which would tend to inactivate the lipase. The reaction of the oat seeds with the triglyceride reactant is preferably carried out at a higher temperature, such as a temperature within the range from 30° to 50° C., with the temperature being controlled to avoid substantial inactivation of the lipase. As the reaction temperature approaches 50° C., some inactivation of the lipase may occur, and temperatures above 50° C. are generally undesirable as causing too much inactivation. Preferably, the reaction temperature is in the range from 35° to 45° C., such as 38° to 40° C.

In carrying out the process, the moistened oat caryopses are contacted with a liquid medium composed essentially of an oil phase containing a fatty acid triglyceride reactant as the principal component. The liquid medium may be composed entirely of the triglyceride reactant unless it is necessary to solubilize or reduce the viscosity of the reactant. If required, a suitable solvent such as hexane can be added.

The reaction contacting can be carried out on a batch or continuous basis. For example, on a batch basis, the reaction container can be charged with the moistened oat caryopses and the reactant, and left in contact for the required time to perform the hydrolysis, means being provided for controlling the temperature of the reaction mixture. For batch reaction the preferred ratio of triglyceride to caryopses is from about 130 to 175 parts by weight of medium per 100 parts caryopses, such as, for example, 155 parts by weight triglyceride to 100 parts caryopses. Other ratios, however, can be used.

The reaction can be accelerated by agitating the oat caryopses in the liquid medium, but the agitation should be sufficiently gentle that the oat seeds are not physically degraded. It is desirable to maintain the oat caryopses in as intact a condition as possible while obtaining thorough contact of the exterior surfaces of the oat caryopses with the triglyceride reactant.

The hydrolysis reaction proceeds slowly. For example, to obtain hydrolysis of 20 to 30% of the triglyceride reactant in the batch-type reactor, contact times of from 5 to 8 days, or longer, may be required. However, since there is little tendency for microbiological deterioration of the oats when immersed in the triglyceride reaction medium, the reaction can be continued as long as required.

In the practice of the method of the invention, the contacting of the oat caryopses with the reaction medium should be continued until at least 20% by volume of the triglyceride reactant has been hydrolyzed to free fatty acids and glycerol. As the extent of hydrolysis increases above 20% up to about 30%, the rate of hydrolysis may decrease. This is apparently due to an inhibition of the lipase by the products of the reaction. To carry the hydrolysis above 30%, it is preferred to remove the used oat caryopses and add a fresh batch of oat caryopses. By using successive batches of oats in this manner, the hydrolysis can be carried to at least 50% of the oil. In optimized embodiments from 75 to 90% or higher percent of the oil can be hydrolyzed.

In the system described, the mechanism of the reaction has advantageous consequences. In effect, each oat caryopses functions as a self-contained bioreactor. There is an internal water phase which extends to the surface of the oat caryopses, where it comes in contact with the external oil phase containing the triglyceride reactant. This provides an oil-water interface around each caryopses. Since the lipase is concentrated near the outer surfaces of the caryopses, bound enzyme is present near the oil-water interface. A further consequence is that the glycerol produced in the reaction tends to be preferentially absorbed within the caryopses, while the fatty acids produced in the reaction disperses into the external oil phase. This partitioning occurs automatically and continuously as the contacting is carried out. At the conclusion of the contacting, as much as 90% of the glycerol may be contained within the caryopses, while as much as 95% of the fatty acids are in the external oil phase.

It has been found that the oat lipase hydrolyzes all three positions of glycerol. Consequently, there is little accumulation of mono- or di- glyceride in the lipid phase. Varieties do vary significantly in the amount of lipase they contain. For the purpose of this invention, it is therefore desirable to select a variety in which the caryopses provide a high content of lipase. The reaction can be accelerated by adding additional lipase, either from oats or other sources.

When it is desired to terminate the reaction, the glycerol containing caryopses can be separated from the liquid phase by centrifugation or filtration. The glycerol can be extracted with water from the caryopses and recovered by distillation. The glycerine-extracted caryopses can be reused in the process, or disposed of as an animal feed material. After separation of the oil phase, it can be processed to recover the fatty acids, for example, by fractional distillation. The oil phase can be subjected to further oat seed hydrolysis, either with or without removal of the fatty acids formed in the prior contacting. Preferably the hydrolysis is continued until at least 30% and preferably over 50% of the oil has been converted into the free acids. Analyses of the product to the reaction has indicated that the oil phase contains very little mono- or di-glycerides. Apparently the hydrolysis proceeds to substantial completion, that is, all of the fatty acids are removed from the glyceride esters.

The process may also be carried out on a continuous or recycle basis. For example, oil may be supplied from an elevated storage tank and introduced into the top of a contacting vessel, the oil being permitted to percolate slowly down through the moistened oat seeds until it is removed from the bottom of the reaction vessel. Means are provided to control the temperature of the feed and in the contacting. For example, water heating jackets can be provided around the storage tank and reaction vessel.

The oil removed from the reaction vessel can be pumped back into the supply tank to continue the contacting on a recycle basis. After the oil has hydrolyzed to the extent of 25 to 30%, the oil from the supply tank can be directed into a second reaction vessel and percolated slowly therethrough as in the first reactor. In this way, fresh batches of oats can be successively contacted with the oil, and the conversion can be carried to higher levels of hydrolysis, such as from 50 to 90% or higher. In another arrangement for continuous processing, the moistened caryopses may be released in a column equipped with a water jacket to maintain the desired water temperature. The triglyceride reactant (the liquid phase) can be pumped into the bottom of the column, passing upwardly through the caryopses to achieve gentle stirring. For passing through the column, the liquid reactant can be passed through a storage tank and from there recycled by pumping back to the bottom of the column. When the reaction is completed, the residual oil may be drained from the caryopses in the column and the caryopses washed with water.

Procedures for practicing the present invention are further illustrated by the following examples.

EXAMPLE I

Dehulled oats are placed in a vessel and mixed with about 20% of their weight of water. After the water has been absorbed by the oats, they are covered with soybean oil. This requires approximately 1.55 units of oil/unit of oats by weight. Temperature is maintained at about 37° C. Hydrolysis is monitored by measuring free fatty acids. When the desired degree of hydrolysis has occurred (approximately 30%), the oil is drained. A fresh batch of dehulled oats are treated with 20% water, and the oil that is about 30% hydrolyzed is added to the fresh oats. When hydrolysis has reached about 60%, the oil is again transferred to a fresh batch of dehulled oats. The reaction is continued until the desired percentage of hydrolysis is attained. The glycerol can be recovered from the batches of used caryopses by soaking them in water, removing the water phase and evaporating it.

EXAMPLE II

The procedure is like Example I, except gentle agitation is used to speed reaction. The moist oat caryopses are packed into a reaction column. The column is filled with soybean oil, and to achieve faster reaction the oil is drained from the bottom of the column and recirculated to the top of the column. Alternatively, oil may be pumped into the bottom of the column and removed from the top, thereby providing gentle agitation for the caryopses.

EXAMPLE III

The procedure is like Example I, except that dilution with hexane is used to decrease the viscosity of the oil and increase reaction rates. An amount of hexane equal to the volume of the oil is used. The ratio of hexane to oil can vary over a wide range, for example, about 10 parts by weight of hexane per 100 parts of oil up to 200 parts of hexane per 100 parts of oil.

We claim:

1. The process for enzymatic hydrolysis of fatty acid triglycerides to obtain free fatty acids and glycerol, comprising the steps of:
   (a) increasing the water content of dehulled whole oat caryopses to a total water content of 17 to 44%, the thus moistened caryopses having active oat lipase associated with the outer surfaces thereof;
   (b) contacting the moistened whole caryopses with a liquid medium composed essentially of an oil phase containing a fatty acid triglyceride reactant as the principal component, said contacting being carried out at a temperature at which the oat lipase is enzymatically active;
   (c) continuing said contacting until at least 20% by volume of the triglyceride reactant has been hydrolyzed to free fatty acids and glycerol, most of the free fatty acids dissolving in the oil phase external to the caryopses and most of the glycerol being absorbed into the water within the caryopses; and
   (d) separating the glycerol-containing caryopses from the fatty acid-containing oil phase.

2. The process of claim 1 in which said triglyceride reactant is a vegetable oil.

3. The process of claim 1 in which said contacting is carried out at a temperature of from 30° to 50° C.

4. The process of claim 1 in which said moistened oat caryopses are substantially saturated with water.

5. The process of claim 1 in which said contacting is carried out with a series of increments of said moistened oat caryopses, and is continued until at least 50% by volume of the triglyceride reactant has been enzymatically hydrolyzed to free fatty acids and glycerol.

6. The process for enzymatic hydrolysis of a vegetable oil to obtain free fatty acids and glycerol, comprising the steps of:
   (a) increasing the water content of dehulled whole oat caryopses to a total water content of 30% by weight up to water saturation thereof, the moistened caryopses thus obtained having active oat lipase bound to the outer surfaces thereof;
   (b) contacting the moistened whole caryopses substantially free of external water with a liquid phase composed essentially of a vegetable oil reactant, said contacting being carried out at a temperature of from 35° to 45° C.;
   (c) continuing said contacting until at least 50% by volume of the vegetable oil reactant has been enzymatically hydrolyzed to free fatty acids and glycerol, substantially all of the free fatty acids dissolving in the oil phase external to the caryopses, and most of the glycerol being absorbed into the water within the caryopses; and
   (d) separating the glycerine-containing caryopses from the fatty acid-containing oil phase.

7. The process of claim 6 in which said moistened oat caryopses are substantially saturated with water.

8. The process of claim 6 in which said contacting is carried out successively with a series of increments of said moistened oat caryopses, and is continued until at least 75% by volume of the vegetable oil reactant has been enzymatically hydrolyzed to free fatty acids and glycerol.

9. The process of claim 1 or claim 6 in which the fatty acids of the triglyceride reactant contain from 4 to 22 carbons.

10. The process of claim 1 or claim 6 in which the fatty acids of the triglyceride reactant contain essentially from 8 to 18 carbons.

* * * * *